United States Patent [19]

Felix et al.

[11] Patent Number: 5,167,638
[45] Date of Patent: Dec. 1, 1992

[54] SUBCUTANEOUS MULTIPLE-ACCESS PORT

[75] Inventors: Augustus Felix, Providence; Arthur L. Rosenthal, Cranston, both of R.I.

[73] Assignee: C. R. Bard, Inc., Murray Hill, N.J.

[21] Appl. No.: 728,834

[22] Filed: Jul. 9, 1991

Related U.S. Application Data

[63] Continuation of Ser. No. 428,127, Oct. 27, 1989, abandoned.

[51] Int. Cl.⁵ .............................................. A61M 5/32
[52] U.S. Cl. .................................. 604/175; 604/244; 604/283
[58] Field of Search ............. 604/86, 88, 93, 173–175, 604/244, 283

[56] References Cited

U.S. PATENT DOCUMENTS

| | | | |
|---|---|---|---|
| 4,673,394 | 6/1987 | Fenton, Jr. et al. | 604/175 |
| 4,692,146 | 10/1987 | Hilger | 604/93 |
| 4,695,273 | 10/1987 | Brown | 604/173 |
| 4,710,174 | 12/1987 | Moden et al. | 604/175 |
| 4,762,517 | 8/1988 | McIntyre | 604/283 |
| 4,767,410 | 8/1988 | Moden et al. | 604/175 |
| 4,772,270 | 10/1988 | Wiita et al. | 604/175 |
| 4,778,452 | 10/1988 | Moden et al. | 604/93 |
| 4,781,680 | 11/1988 | Redmond et al. | 604/86 |
| 4,886,501 | 12/1989 | Johnston et al. | 604/93 |
| 4,892,518 | 1/1990 | Cupp et al. | 604/93 |
| 4,915,690 | 4/1990 | Cone et al. | 604/175 |
| 4,929,236 | 5/1990 | Samson | 604/175 |

Primary Examiner—John D. Yasko
Assistant Examiner—Anthony Gutowski
Attorney, Agent, or Firm—Wolf, Greenfield & Sacks

[57] ABSTRACT

A multiple chamber subcutaneously implantable infusion port and catheter assembly is formed from a small number of plastic components that are easily injection molded and assembled. The components are constructed so that a catheter assembly is easily and securely bonded to the port.

16 Claims, 2 Drawing Sheets

SUBCUTANEOUS MULTIPLE-ACCESS PORT

This application is a continuation of application Ser. No. 07/428,127, filed Oct. 27, 1989, now abandoned.

FIELD OF INVENTION

This invention relates to subcutaneously implanted, infusion ports for the infusion of medicine and, more particularly, to a multiple port device and a method for its manufacture.

BACKGROUND OF THE INVENTION

Implantable, subcutaneous infusion ports are designed to provide an easily accessible means to deliver medication to a body lumen or cavity such as a blood vessel. Such devices are used, for example, to deliver a predetermined amount of medication into the patient s blood vessel. They are intended for long term use. Such ports typically include an injection chamber, which is accessible, percutaneously, through a pierceable septum. The chamber is connected to a catheter, which also is subcutaneously placed and leads to the body lumen to which the medication is to be delivered. The device is designed to be implanted just beneath the skin so that the chamber may be accessed repeatedly by passing a hypodermic needle through the skin and septum.

Patients often require the infusion of more than one type of medication. The medications frequently may be incompatible. For example, mixing different, incompatible drugs may cause crystallization or occlusion of the lumen of the delivery catheter in a single chamber implantable infusion port. Additionally, blood sometimes must be withdrawn while simultaneously infusing medication. The use of a multiple chamber infusion port with a multiple lumen catheter or a plurality of catheters facilitates such simultaneous multiple uses. Typical of such chamber dual chamber vascular access ports is that shown in U.S. Pat. No. 4,692,146. That access port has an anchoring base made of a flexible biocompatible such as silicone rubber. Two separate stainless steel ports are enclosed in the base and define chambers for medication or the like. Each of the ports is formed from a number of separate parts that are separately machined and assembled. Each port has a piercable septum and a circular stop to prevent a needle from protruding too far into the chamber after puncturing the septum. The catheter that is connected to each port is provided with a metal tube inside of the catheter where the port is attached in order to prevent the needle from inadvertently puncturing the catheter and causing it to leak. Such access ports typically have a considerable number of parts and required a substantial amount of labor for their manufacture. The use of metal components increases the weight of the implantable infusion port and may be somewhat uncomfortable for the patient. Also, a device having metal components will interfere with Magnetic Resonance Imaging ("MRI"), which is often used for diagnostic procedures. There is a need, therefore, for an improved, non-metallic subcutaneously implantable multiple chamber infusion port that is of simplified, inexpensive construction.

SUMMARY OF THE INVENTION

In accordance with the invention, an implantable, multiple-chamber infusion port includes a molded plastic base formed to include the plurality of chambers. A septum is disposed at the top of each chamber and a top piece formed from molded plastic fits over the top of the base and engages the septums while covering the base. Each of the chambers is associated with a nipple that extends from the base and communicates with one of the chambers. A multiple lumen catheter assembly is connected to the nipples. The nipples include a plurality of irregular elements and the base has crevices and irregularly shaped portions adjacent the nipples. The nipples protrude into a recess defined by openings in the assembled top and base. The catheter assembly includes a hub by which attaches to the nipples and communicates each of the nipples with one lumen of the catheter. The hub also is disposed, in part, within the recess. After the hub of the catheter assembly has been attached to the nipples, a silicone compound is injected into the recess. The injected silicone fuses to the catheter hub and mechanically interlocks with irregularities on the inside of the recess to lock securely the catheter assembly to the base and nipples.

The multiple infusion port of the invention is very simple to manufacture and assemble. The device is a leak-proof, non-metallic, has fewer parts than other subcutaneous infusion ports, requires no machining of parts and is considerably less expensive to manufacture than other such devices. The multiple infusion port of the invention may be made entirely from plastic and silicone compounds, and, thus, is lightweight so that it is easier for the patient to become accustomed to it. Other objects, features and advantages of the invention will become apparent when the following portions of the specifications are read in conjunction with the accompanying drawings.

DESCRIPTION OF THE PREFERRED EMBODIMENT

The present invention relates to a subcutaneous, multiple chamber port and method for its manufacture. Although the following description refers to a dual-chamber port the invention is equally applicable to multiple-chamber ports containing more than two access ports.

Figure 4:
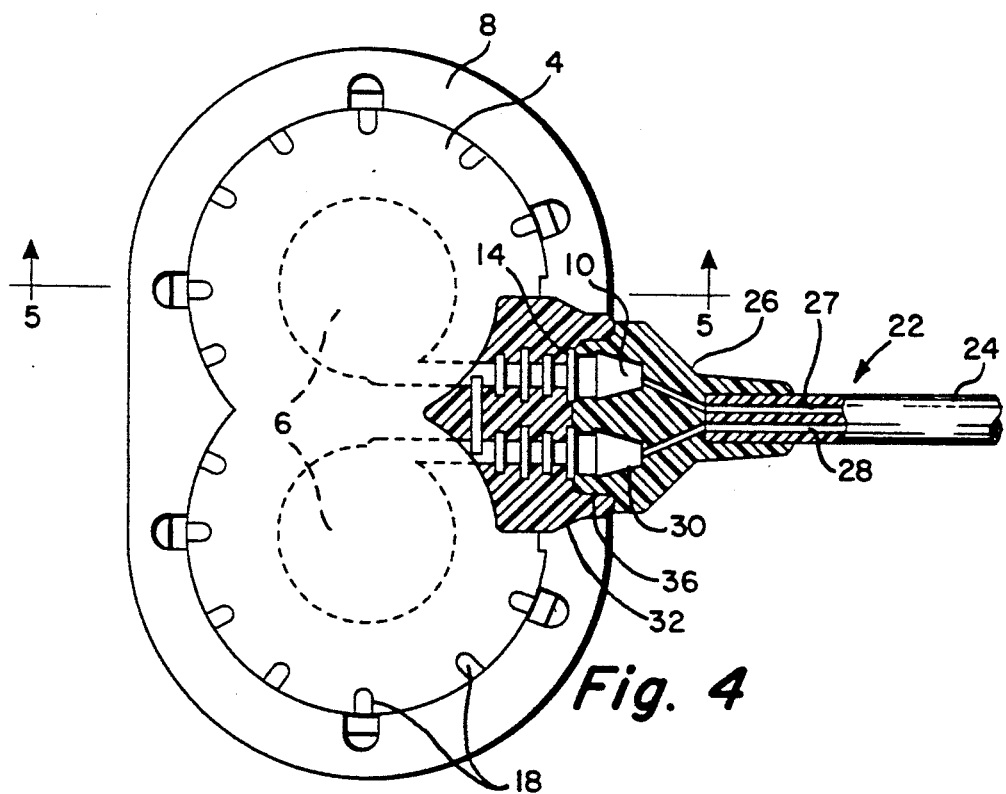
FIG. 4 is a partially plan, partially cut-away view of the port of the invention, as taken along line 4—4 of FIG. 3.
Figure 5:
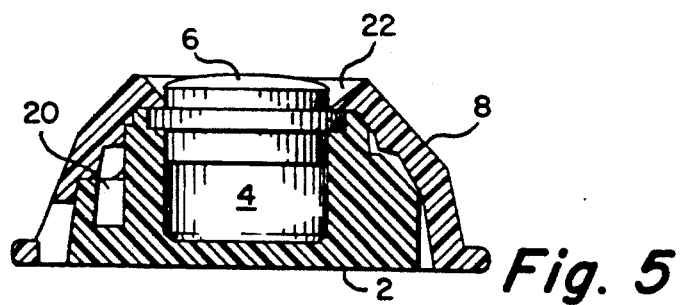
FIG. 5 is a sectional view of the port taken along line 5—5 of FIG. 4.

Referring to the drawings, the device according to the invention includes an injection molded plastic base 2 which is formed to have a pair of chambers 4, most clearly seen in FIG. 5. Each chamber 4 is enclosed by a septum 6 which defines the top of the chamber. A top piece 8 also is formed from injection molded plastic, and fits over the base 2, so as to engage the septums 6 and secure them in place while covering the base 2. As can be most clearly seen in FIGS. 2 and 4, the base 2 includes a pair of integrally formed nipples 10, each of which communicates with one of the two chambers 4.

Figure 1:
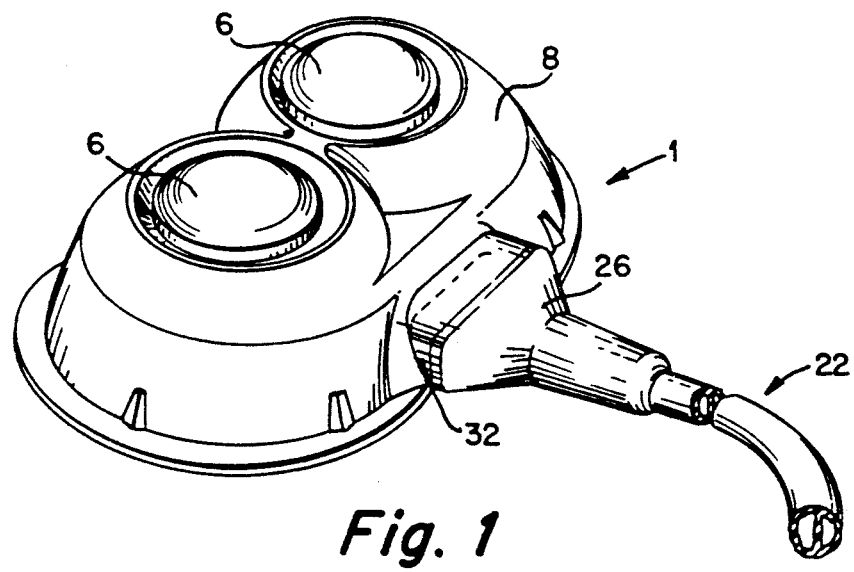
FIG. 1 is a perspective view of a dual subcutaneous, port embodying the invention.
Figure 2:
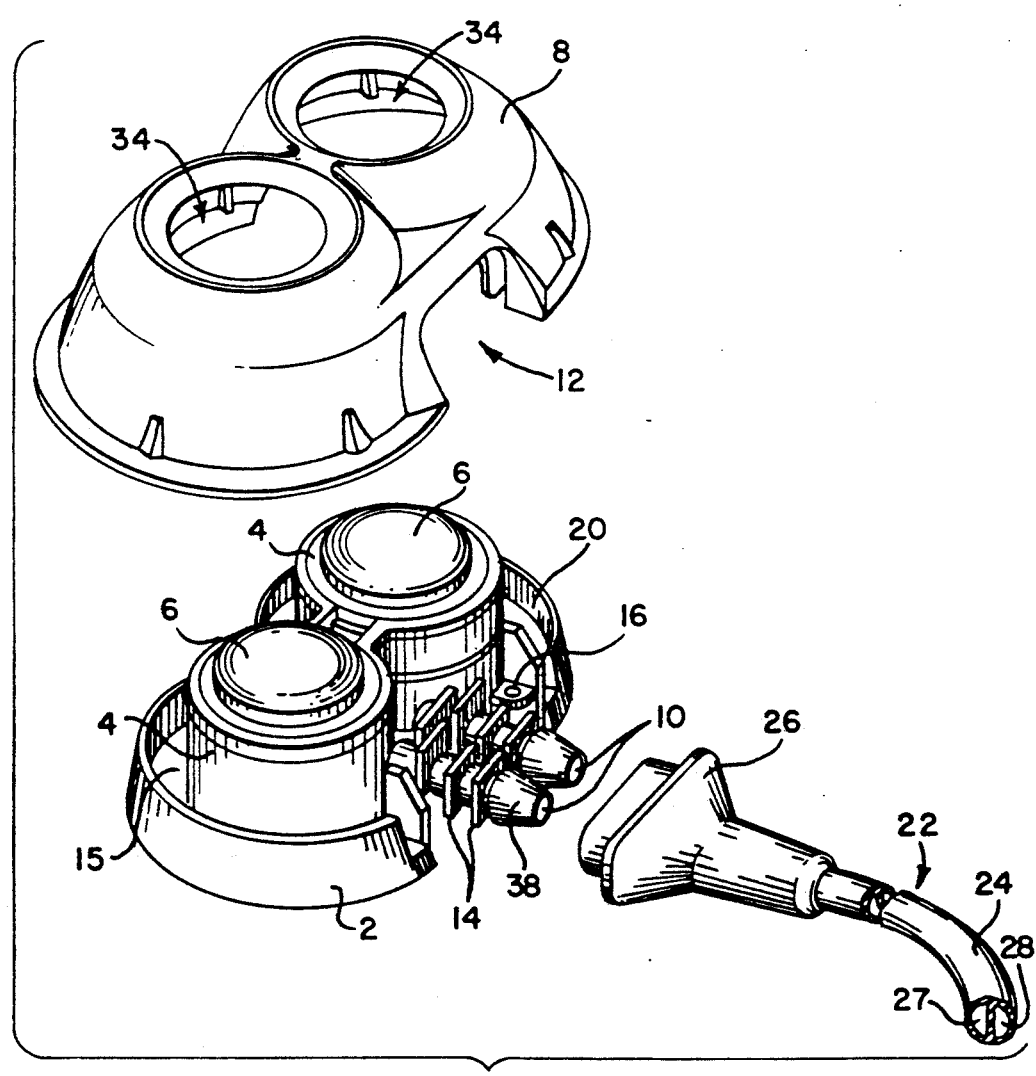
FIG. 2 is an exploded view of the port shown in FIG. 1.
Figure 3:
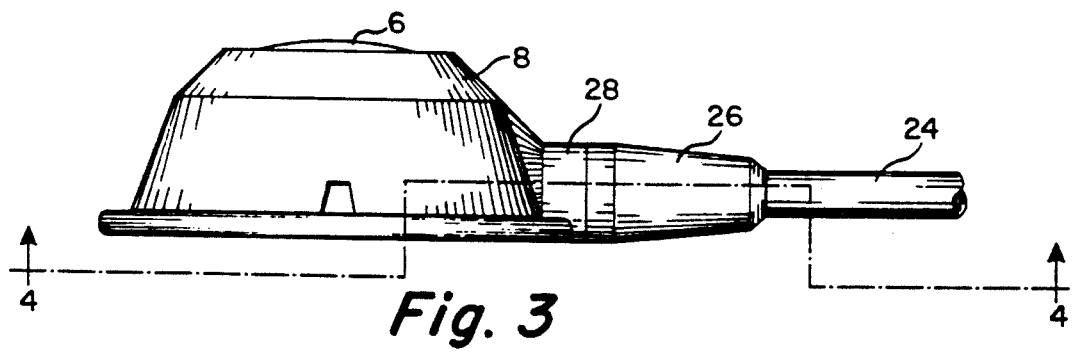
FIG. 3 is a side view of the port shown in FIG. 1.

The top piece 8 has an opening 12, which fits around the nipples 10, forming a recess at the underside of the device in cooperation with the base. When the base 2 and the top 8 are assembled the nipples 10 are exposed in the recess defined by the opening 12, as can be most clearly seen from the underside of the device as shown in FIG. 4. The nipples 10 have a plurality of integrally molded irregular fin-like elements 14 that protrude therefrom and elements 14 extend in a direction transverse to the axes of the nipples 10. The base 2 further includes irregularly shaped portions 16, as shown in FIG. 2 which have holes formed therein. In addition, the top 8 has projections 18 which protrude from the inner side of the top 8 into an outer channel 20 in the base disposed outside chambers 4. The irregular elements 14, portions 16 and projections enhance the attachment of the catheter assembly, as will be described. The top 8 and the base 2 are made of implantable grade plastic such as Delrin TM which is impervious to piercing by a hypodermic needle.

The base 2 with the chambers 4, irregularly-shaped portions 16, nipples 10 and irregular elements 14 all are formed from a single piece of plastic made by either injection molding or by transfer mold processing. Thus, when assembling the device, the base 2 and top 8 are brought together to capture the septums 6, and the base 2 and top 8 are united, for example, by ultrasonic welding. This assembly is then attached to a catheter assembly 22, which includes an elongated silicone rubber dual lumen catheter tube 24 having a silicone rubber hub 26 at one end. The catheter assembly 22 preferably has two D shaped lumens 27 and 28. Referring to the bottom view of FIG. 4, the hub 26 has a pair of sockets 30 which are arranged to receive the protruding ends of the nipples 10. The sockets 30 communicate with the two lumens 27 and 28 within the catheter 24. Once the base and top are united together, the silicone hub 26 is connected to the nipples 10 so that the hub 26, the base 2 and the top 8 define the recess. The recess then is injected with a potting material such as a silicone rubber compound, shown in FIG. 4. This potting material 32 fuses to the catheter hub 26, while simultaneously mechanically interlocking with the irregularities 16 on the base 2, the irregular elements 14 protruding from the nipples 10 and the projections 18 on the inner side of the top 8.

The irregular elements 14 protruding from the nipples 10 include frusto-conical protrusions at the ends of the nipples 10 farthest from the base 2 with the base of the frusto conical protrusions facing the base 2. The hub 26 has a pair of ridges, each of which projects inwardly toward the axis of its respective socket 32. The ridges interlock with the frusto-conical protusions of the nipples 10 to further secure the hub 26 to the base 2 prior to and during the injection of potting material 32.

The manufacturing process of the dual-access port of the invention is fairly simple. First, the septums 6 are inserted to the tops of the chambers 4 which are integrally formed in the base 2. Once this is completed, the top 8 is placed over the base 2, so that the septums 6 are rigidly held in place. At the same time, the upper surfaces of the septums 6 are exposed through openings 34 in top 8, thus permitting access to the chambers 4 via a needle during use. After the top 8 and base 2 are united by ultrasonically welding the catheter assembly 22 is attached to the base so that the hub 26 of the catheter assembly 22 is connected via sockets 30 to the end portions of nipples 10. As seen in FIG. 4, the sockets 30 have a smaller diameter portion 36, which projects inwardly to engage the conical tops 38 of the nipples 10, and thus maintain the hub 26 in fixed relation to the base 2.

Once the catheter assembly 22 has been connected, the entire assembly is placed in a mold (not shown) and the potting material 32 is injected into the recessed portion formed by the base 2, the opening 12 in the top piece 8 and the hub 26. As the potting material 32 solidifies, it fuses to the catheter hub 26 and thus, mechanically interlocks with the irregularities 16 on the inside of the recessed portions, the irregular elements 14 protruding from the nipples 10 and the projecting pieces 18. Consequently, the catheter hub 26 is securely locked to the base 2 and the nipples 10. Since the potting material is in a liquid state during injection it flows into the crevices formed by the irregularities 16, irregular elements 14 and projections 18. The potting material flows through the holes in the irregularities 16 to anchor the hub 26 when the potting material solidifies.

The device, so constructed, is very simple to manufacture and assemble. The process requires a minimal number of steps and utilizes parts which are easily manipulated. The base 2 and the top 8 may be made from a hard plastic such as Delrin TM which is resistant to penetration by a needle. The resulting device is leak proof. It has fewer parts than other subcutaneous dual ports. No machining of the parts is required, thus simplifying the manufacturing process and achieving manufacturing economies. The manufacture of the dual port device entirely from plastic and potting materials such as silicone compounds reduces the overall weight of the device and it is relatively easy for a patient to become accustomed to the device once it is implanted, since the weight of the present device is much less than other subcutaneous ports. A further advantage that results from the manufacture of the device from an all-plastic construction, is that it does not affect MRI procedures as does a device having metal components. By providing the catheter assembly 22 with a hub 26 having sockets 30, it is a relatively simple matter to connect both lumens 27 and 28 to their respective nipples 10 in a single operation and then to secure the assembly together with a simple injection of silicone rubber.

The hub 26 is formed by injecting potting material into a mold, which conforms to the shape of the hub 26, and simultaneously attaching the catheter tube 24 so that the hub 26 and catheter tube 24 are bonded together as the hub solidifies.

As mentioned previously, the present invention is equally applicable to the case where more than two access ports are utilized or where a single port is employed. While the embodiments shown in FIGS. 1-5 show the protrusions 14 on the nipples 10 being transverse to the access of the nipples 10, these protrusions may, in fact, protrude in other directions so long as they facilitate the interlocking of the hub 26 of the catheter assembly 22 to the base 2 via the injection of the potting material 32. While a preferred embodiment of the present invention has been disclosed, it will be appreciated by one skilled in the art that it does not limit the invention, which may otherwise be embodied within the scope of the following claims:

What is claimed is:

1. A subcutaneously implantable multiple port and preattached catheter comprising:
    a base having a plurality of open ended chambers, an externally exposed recess and a plurality of hollow nipples in communication with and extending from said chambers, said nipples being integral with said base and protruding into the recess;

a pierceable septum, covering the open end of each chamber;

a top member attached to and covering the base, the top member engaging the septums while exposing the septums;

a catheter assembly including a multi-lumen catheter connected at one end to said nipples, with a lumen in communication with each nipple, the connection being disposed within the recess; and the recess being filled substantially in its entirety with a potting material to encapsulate the connection between the catheter assembly and the nipples and to form a permanent connection of the catheter to the base.

2. A subcutaneous port as recited in claim 1, wherein said base and said top portion are made of a relatively rigid plastic.

3. A subcutaneous port as recited in claim 1, wherein said nipples have a plurality of protrusions extending therefrom, the potting material filling the spaces between the protrusions thereby to form a mechanical interlock between the potting material and the protrusions.

4. A subcutaneous port as recited in claim 1 wherein said base further comprises a plurality of protrusions extending into said recess and embedded in the potting material.

5. A subcutaneous port as recited in claim 4, wherein said catheter assembly has a hub at one end, the catheter and hub being formed from the same material as the potting material whereby the hub of the catheter assembly and the potting material may form a unitary fused structure.

6. A subcutaneous port as recited in claim 5, wherein said hub includes a pair of sockets disposed to receive the nipples each of said sockets communicating with one of said catheter lumens.

7. A subcutaneous port as recited in claim 6, wherein said hub catheter and potting material are formed from silicone rubber.

8. A subcutaneous port as recited in claim 5, wherein said top portion further comprises projections extending from an inner surface of said top portion such that said potting material mechanically interlocks with said projections.

9. A subcutaneous port as recited in claim 5, wherein said protrusions have holes disposed therein such that said potting material extends through said holes.

10. A subcutaneous port as defined in any one of claims 1-9 wherein there are two of said chambers.

11. A catheter assembly, as recited in claim 6, wherein said hub further comprises ridges disposed near open ends of said sockets, each of said ridges projecting inwardly, toward an axis of one of said plurality of sockets, so as to engage said nipples of said base.

12. A subcutaneously implantable device having at least one port and a preattached catheter, comprising:

a base having at least one open ended chamber, an externally exposed recess, at least one hollow nipple in communication with and extending from said at least one chamber and protruding into said recess, said at least one nipple being integral with said base;

at least one pierceable septum, covering the open end of said at least one chamber;

a top member attached to and covering said base, said top member engaging said at least one septum while exposing said at least one septum;

a catheter assembly, including a catheter having at least one lumen, connected to at one end to said at least one nipple, with said at least one lumen in communication with said at least one nipple, said connection being disposed in said recess; and said recess being filled substantially in its entirety with a potting material to encapsulate said connection between said catheter assembly and said at least one nipple said potting material being fused to the catheter while simultaneously mechanically interlocking with at least one of the components within the recess selected from the group consisting of irregularities on the base, irregular elements on the nipples and projections on the inner side of the top thereby to form a permanent connection of the catheter to the base.

13. A subcutaneous port as recited in claim 1 wherein the potting material is placed into the recess in a flowable state and subsequently solidifies.

14. A subcutaneous port or device as recited in claims 12 or 13, wherein the catheter assembly includes a catheter hub and the potting material fuses to the catheter hub upon solidification.

15. A subcutaneous port or device as recited in claim 1 wherein the potting material mechanically interlocks with at least one of the components within the recess selected from the group consisting of irregularities on the base, irregular elements on the nipples and projections on the inner side of the top.

16. A subcutaneously implantable multiple port and preattached catheter as defined in any one of claims 1 through 9, 11 or 12 further comprising:

said port being substantially free of metallic elements.

* * * * *